United States Patent
Nimmagadda et al.

(10) Patent No.: US 10,391,324 B2
(45) Date of Patent: *Aug. 27, 2019

(54) SELECTABLE BOOST CONVERTER AND CHARGE PUMP FOR COMPLIANCE VOLTAGE GENERATION IN AN IMPLANTABLE STIMULATOR DEVICE

(71) Applicant: Boston Scientific Neuromodulation Corporation, Valencia, CA (US)

(72) Inventors: Kiran Nimmagadda, Valencia, CA (US); Md. Mizanur Rahman, Valencia, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/847,641

(22) Filed: Dec. 19, 2017

(65) Prior Publication Data
US 2018/0104498 A1 Apr. 19, 2018

Related U.S. Application Data

(60) Continuation of application No. 14/988,188, filed on Jan. 5, 2016, now Pat. No. 9,872,995, which is a (Continued)

(51) Int. Cl.
*A61N 1/378* (2006.01)
*H02M 3/07* (2006.01)
(Continued)

(52) U.S. Cl.
CPC .......... *A61N 1/3782* (2013.01); *A61N 1/378* (2013.01); *A61N 1/37211* (2013.01); *H02M 3/07* (2013.01);
(Continued)

(58) Field of Classification Search
CPC ............ A61N 1/36125; A61N 1/36153; A61N 1/37252; A61N 1/37223; A61N 1/3727; A61N 1/37276; A61N 1/37282
See application file for complete search history.

(56) References Cited

U.S. PATENT DOCUMENTS

| 5,733,313 A | 3/1998 | Barreras et al. |
| 5,757,167 A | 5/1998 | Aurora et al. |

(Continued)

FOREIGN PATENT DOCUMENTS

| EP | 1686692 | 8/2006 |
| WO | 99/52163 | 10/1999 |

(Continued)

OTHER PUBLICATIONS

Pylarinos, Louie, "Charge Pumps: An Overview" in *Proceedings of the IEEE International Symposium on Circuits and Systems*, 2003.
(Continued)

*Primary Examiner* — Alyssa M Alter
(74) *Attorney, Agent, or Firm* — Lewis & Reese, PLLC

(57) ABSTRACT

Compliance voltage generation circuitry for a medical device is disclosed. The circuitry in one embodiment comprises a boost converter and a charge pump, either of which is capable of generating an appropriate compliance voltage from the voltage of the battery in the device. A boost signal from compliance voltage monitor-and-adjust logic circuitry is processed with a telemetry enable signal to selectively enable either the charge pump or the boost converter: if the telemetry enable signal is not active, the boost converter is used to generate the compliance voltage; if the telemetry enable signal is active, the charge pump is used. Because the charge pump circuitry does not produce a magnetic field, the charge pump will not interfere with magnetically-coupled telemetry between the implant and an external controller. By contrast, the boost converter is allowed to operate during
(Continued)

periods of no telemetry, when magnetic interference is not a concern.

17 Claims, 10 Drawing Sheets

Related U.S. Application Data division of application No. 12/372,501, filed on Feb. 17, 2009, now Pat. No. 9,233,254.

(51) Int. Cl.
*H02M 3/156* (2006.01)
*A61N 1/372* (2006.01)
*H02M 1/00* (2006.01)

(52) U.S. Cl.
CPC ...... *H02M 3/156* (2013.01); *H02M 2001/009* (2013.01)

(56) References Cited

U.S. PATENT DOCUMENTS

| | | | |
|---|---|---|---|
| 5,814,089 A | 9/1998 | Stokes et al. | |
| 5,818,703 A | 10/1998 | Jacobson | |
| 5,847,551 A | 12/1998 | Aurora et al. | |
| 6,289,246 B1 | 9/2001 | Money | |
| 6,370,046 B1 | 4/2002 | Nebrigic et al. | |
| 6,429,632 B1 | 8/2002 | Forbes et al. | |
| 6,516,227 B1 | 2/2003 | Meadows et al. | |
| 6,525,949 B1 | 2/2003 | Johnson et al. | |
| 6,631,296 B1 | 10/2003 | Parramon et al. | |
| 6,668,193 B2 | 12/2003 | Ware et al. | |
| 6,704,597 B1 | 3/2004 | Ware et al. | |
| 6,826,430 B2 | 11/2004 | Faltys et al. | |
| 6,873,874 B2 | 3/2005 | Ware et al. | |
| 7,079,900 B2 | 7/2006 | Greenburg et al. | |
| 7,151,963 B2 | 12/2006 | Havel et al. | |
| 7,200,434 B2 | 4/2007 | Havel et al. | |
| 7,203,539 B2 | 4/2007 | Ware et al. | |
| 7,203,549 B2 | 4/2007 | Schommer et al. | |
| 7,263,406 B2 | 8/2007 | Toy et al. | |
| 7,272,445 B2 | 9/2007 | Phillips et al. | |
| 7,444,181 B2 | 10/2008 | Shi et al. | |
| 7,519,428 B1 | 4/2009 | Palmer | |
| 7,805,189 B2 | 9/2010 | Stein et al. | |
| 9,872,995 B2 * | 1/2018 | Nimmagadda | A61N 1/378 |
| 2002/0087196 A1 | 7/2002 | Ware et al. | |
| 2003/0074037 A1 | 4/2003 | Moore et al. | |
| 2003/0125773 A1 | 7/2003 | Havel et al. | |
| 2003/0187484 A1 | 10/2003 | Davis et al. | |
| 2003/0204224 A1 | 10/2003 | Torgerson et al. | |
| 2003/0234631 A1 | 12/2003 | Schulman et al. | |
| 2004/0111123 A1 | 6/2004 | Ware et al. | |
| 2004/0167407 A1 | 8/2004 | Roberts | |
| 2005/0027318 A1 | 2/2005 | Ware et al. | |
| 2005/0075684 A1 | 4/2005 | Phillips et al. | |
| 2005/0075685 A1 | 4/2005 | Forsberg et al. | |
| 2005/0075686 A1 | 4/2005 | Phillips et al. | |
| 2005/0075688 A1 | 4/2005 | Toy et al. | |
| 2005/0075689 A1 | 4/2005 | Toy et al. | |
| 2005/0075690 A1 | 4/2005 | Toy et al. | |
| 2005/0075691 A1 | 4/2005 | Phillips et al. | |
| 2005/0075692 A1 | 4/2005 | Schommer et al. | |
| 2005/0165451 A1 | 7/2005 | Ware et al. | |
| 2005/0228453 A1 | 10/2005 | Havel et al. | |
| 2005/0275382 A1 | 12/2005 | Stessman et al. | |
| 2006/0276857 A1 | 12/2006 | Forsberg et al. | |
| 2007/0016263 A1 | 1/2007 | Armstrong et al. | |
| 2007/0097719 A1 * | 5/2007 | Parramon | A61N 1/378 363/72 |
| 2007/0135868 A1 | 6/2007 | Shi et al. | |
| 2007/0146020 A1 | 6/2007 | Williams | |
| 2007/0208261 A1 | 9/2007 | Maniak et al. | |
| 2007/0212596 A1 | 9/2007 | Nebrigic et al. | |
| 2007/0288068 A1 | 12/2007 | Toy et al. | |
| 2008/0015657 A1 | 1/2008 | Haefner | |
| 2008/0114231 A1 | 5/2008 | Dai et al. | |
| 2008/0127478 A1 | 6/2008 | Phillips et al. | |
| 2009/0018618 A1 | 1/2009 | Parramon et al. | |
| 2009/0024187 A1 | 1/2009 | Erickson et al. | |
| 2009/0043244 A1 | 2/2009 | Iran | |
| 2010/0256712 A1 | 10/2010 | Varrichio et al. | |

FOREIGN PATENT DOCUMENTS

| | | |
|---|---|---|
| WO | 2003/047685 | 6/2003 |
| WO | 2005/042087 | 5/2005 |
| WO | 2005/042092 | 5/2005 |
| WO | 2005/042093 | 5/2005 |
| WO | 2005/042094 | 5/2005 |
| WO | 2005/042095 | 5/2005 |
| WO | 2005/042096 | 5/2005 |
| WO | 2005/042097 | 5/2005 |
| WO | 2005/042098 | 5/2005 |

OTHER PUBLICATIONS

Chebli, Robert, et al., "A Wide Tuning Range Voltage-Controlled Ring Oscillator Dedicated to Ultrasound Transmitter", presented at International Conference on Microelectronics, Dec. 2004.

Sun, et al, "Power Management in a Bio-telemetry Application", Power Electronics Specialists Conference 2005, ISBN: 978-0-7803-9033-1, pp. 1182-1190, Jan. 1, 2005.

International Search Report and Written Opinion regarding corresponding PCT application No. PCT/US2009/063578, dated Feb. 17, 2010.

* cited by examiner

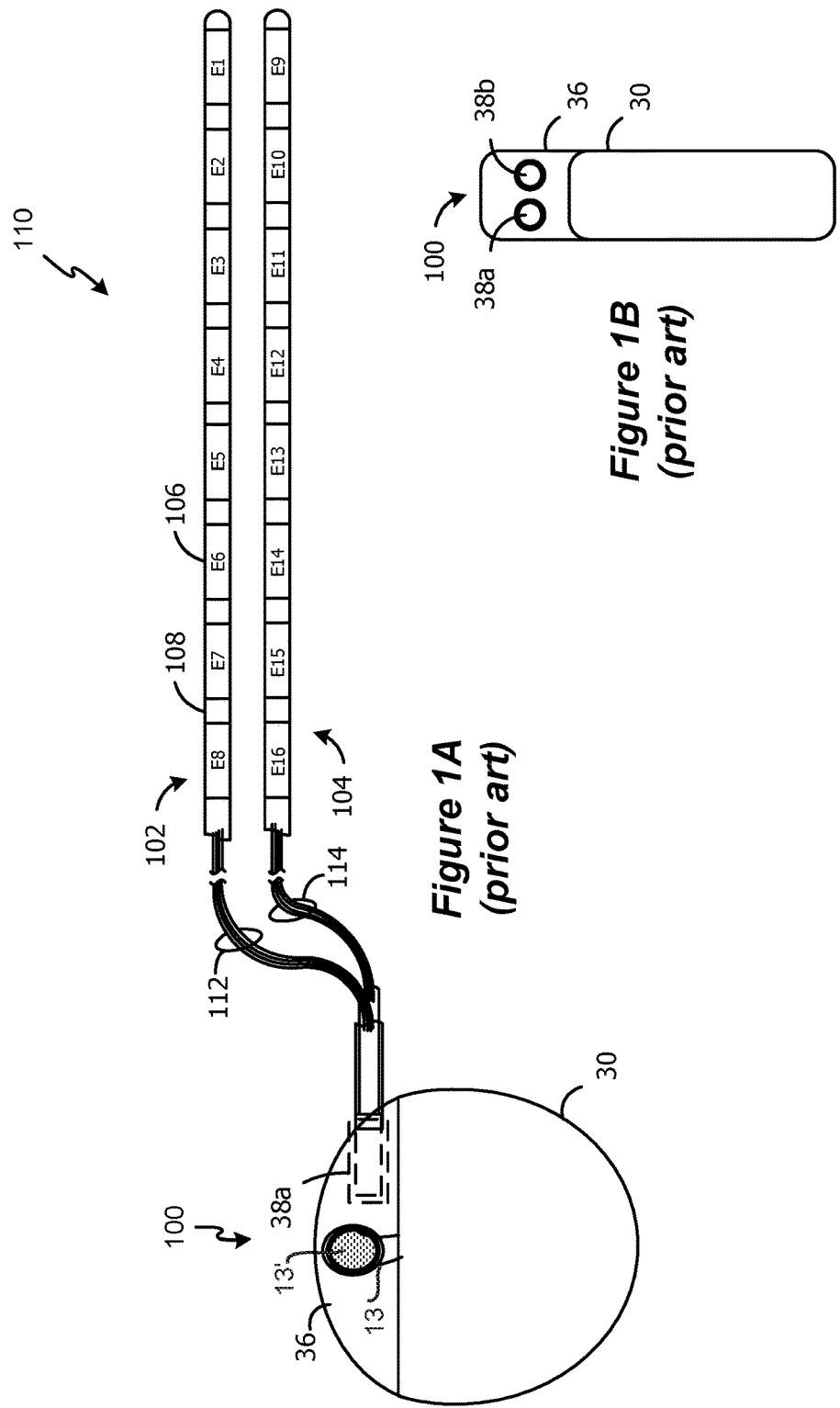
Figure 1A (prior art)
Figure 1B (prior art)

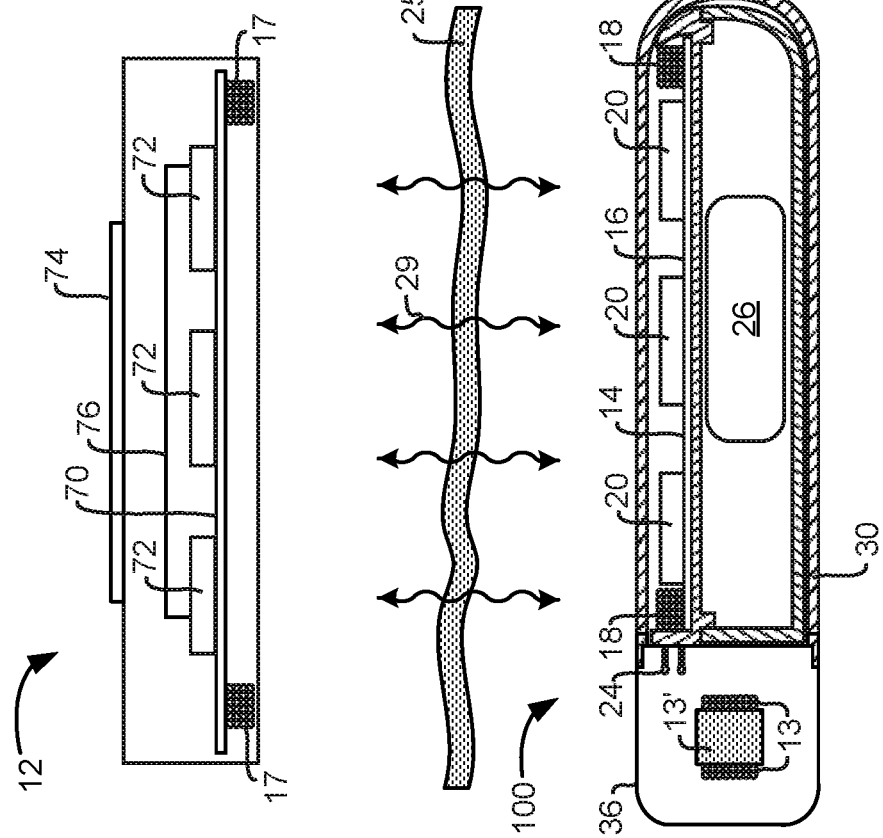

SELECTABLE BOOST CONVERTER AND CHARGE PUMP FOR COMPLIANCE VOLTAGE GENERATION IN AN IMPLANTABLE STIMULATOR DEVICE

CROSS-REFERENCE TO RELATED APPLICATIONS

This is a continuation application of U.S. Non-Provisional patent application Ser. No. 14/988,188, filed Jan. 5, 2016 (allowed), which is a divisional application of U.S. Non-Provisional patent application Ser. No. 12/372,501, filed Feb. 17, 2009 (now U.S. Pat. No. 9,233,254), which are incorporated herein by reference, and to which priority is claimed.

FIELD OF THE INVENTION

The present invention relates to high voltage generation circuitry in an implantable medical device for producing a high stimulation compliance voltage from a battery voltage.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable medical device system. For example, the disclosed invention can also be used with a Bion™ implantable stimulator, such as is shown in U.S. Patent Publication 2007/0097719, filed Nov. 3, 2005, or with other implantable medical devices.

As shown in FIGS. 1A and 1B, a SCS system typically includes an Implantable Pulse Generator (IPG) 100, which includes a biocompatible device case 30 formed of titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102, 104 couple to the IPG 100 using lead connectors 38a and 38b, which are fixed in a header material 36, which can comprise an epoxy for example.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Three coils are generally present in the IPG 100: a telemetry coil 13 used to transmit/receive data to/from an external controller 12; a charging coil 18 for charging or recharging the IPG's battery 26 using an external charger (not shown); and a coil 66 (not shown in FIG. 2) used in the boost converter 150 used to generate a high compliance voltage, as discussed below in conjunction with FIG. 3. The telemetry coil 13 can be mounted within the header 36 of the IPG 100 as shown, or it can be mounted on the printed circuit board within the IPG.

As just noted, an external controller 12, such as a hand-held programmer or a clinician's programmer, is used to send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12.

Wireless data transfer between the IPG 100 and the external controller 12 takes place via magnetic inductive coupling. To implement such functionality, both the IPG 100 and the external controller 12 have telemetry coils 13 and 17. Either coil can act as the transmitter or the receiver, thus allowing for two-way communication between the two devices, as explained further below. When data is to be sent between the external controller 12 and the IPG 100, the transmitting coil 17 or 13 is energized with alternating current (AC), which generates a magnetic field 29, which in turn induces a current in the other of coils 17 or 13. The generated magnetic field 29 is typically modulated using a communication protocol, such as a Frequency Shift Keying (FSK) protocol, which is well known in the art. The power used to energize the coil 17 or 13 can come from batteries 76 and 26 within the external controller 12 and IPG 100 respectively. The induced current in the receiving coil can then be demodulated back into the data signals that were transmitted.

Inductive transmission of data can occur transcutaneously, i.e., through the patient's tissue 25, making it particular useful in a medical implantable device system. During the transmission of data, the coils 13 and 17 preferably lie along a common axis in planes that are parallel. Such an orientation between the coils will generally improve the coupling between them, but deviation from ideal orientations can still result in reliable data transfer.

As shown in FIG. 3, a therapeutic current, Iout, to be provided at a given electrode 106 (only one electrode in shown in FIG. 3 for convenience) is provided by a current source. In the illustrated example, the current source is digitally programmable and is referred to as a Digital-to-Analog Converter, or "DAC" 60. The current is provided to the patent's tissue, R, and is set with respect to a reference potential (e.g., ground) as designated generically by node 107, which may comprise another electrode 106, the case 30 of the IPG 100, etc. The electrode 107 may or may not be coupled to a DAC of its own. For example, if electrode 106 sources Iout, electrode 107 may be programmed to sink Iout to ensure that no charge builds up in the patient's tissue, R.

For the DAC 60 to be able to provide the desired output current, Iout, the DAC 60 must receive a power supply voltage, called the compliance voltage, V+, and which is generated by a boost converter 150. The boost converter 150 comprises one type of DC-DC conversion circuit and is used to convert the battery voltage, Vbat, to the compliance voltage V+. The compliance voltage V+ provides power to the electrodes or other loads in a more generic implantable medical device. The boost converter 150 is needed in an IPG 100 because the compliance voltage, V+, required to provide the desired therapeutic current, Iout, at the electrode may be higher than the battery voltage, Vbat. For example, the battery voltage, Vbat, may be in the neighborhood of 4V, while compliance voltages of 18-20V may be necessary to provide higher-magnitude therapeutic currents.

The compliance voltage V+ is adjustable depending on the power it must provide at any given time. Its optimal value at any given time depends on the magnitude of the programmed stimulation current, the resistance of the tissue R, and other factors. Adjustment of V+ is important in the IPG: if V+ is too low, the DAC 60 will become "loaded" and unable to provide the desired current, Iout; if V+ is too high, the DAC 60 will be able to provide the desired current, Iout, but battery power will be wasted, because some portion of the compliance voltage V+ will be dropped across the DAC 60 without any useful effect.

Adjustment of V+ is made by V+ monitor and adjust logic circuitry 62, which determines whether V+ needs to be raised or lowered via a feedback loop. V+ monitor and adjust logic circuitry 62 can comprise part of the IPG's microcontroller 155 (see FIG. 4), or may be a standalone circuit block. If V+ is too low, circuitry 62 outputs a "boost" signal to a pulse width modulator 63. The pulse width modulator adjusts the pulse width of a clock signal, CLK, in a manner specified by a pulse width, PW, provided by the IPG's microcontroller 155 (FIG. 4). The pulse-width-modulated pulse train is sent to the gate of a transistor 64. When the transistor 64 is on, current passes through an inductor 66, which can comprise a dedicated inductor used exclusively in the boost converter 150, or can comprise one of the coils 18 or 13' (FIG. 2) in the IPG 100. Later, when the transistor 64 is turned off, the current in the inductor 66 must discharge and does so through diode 68 to charging capacitor 69, whose top plate comprises the compliance voltage V+. Because the capacitor 69 was already charged to the battery voltage, Vbat, the additional charge from the inductor 66 boosts the compliance voltage V+ to a value higher than Vbat. Diode 68 prevents this excess charge from dissipating backwards into the circuit, and the capacitor 69, in addition to storing the charge, also filters the compliance voltage to stabilize it. Thus, as the gate of transistor 64 oscillates between on and off, the compliance voltage V+ continues to boost. If V+ monitor and adjust logic circuitry 62 determines that V+ is too high, it disables the "boost" signal. This halts oscillations at the gate of the transistor 64, which causes V+ to fall as charge is consumed by stimulation current delivered by the DAC 60.

Further details concerning boost converter circuitry can be found in U.S. Pat. No. 7,872,884, which is incorporated herein by reference in its entirety. Moreover, one skilled in the art will realize that circuits other than a pulse width modulator 63 can be used in a boost converter. For example, a current- or voltage-controlled ring oscillator could also be used to toggle transistor 64.

While the boost converter 150 functions well to produce the desired compliance voltage V+, the inventors have noticed a shortcoming of such design. Specifically, the boost converter 150 has the potential to interfere with the telemetry circuitry operable in the IPG 100. FIG. 4 illustrates a typical bi-directional telemetry link operable between an IPG 100 and an external controller 12. As shown, the external controller 12 and the IPG 100 respectively contain transmitter/modulation and receiver/demodulation circuitry coupled to their coils 17 and 13 for communicating data between them. When data 170 is to be sent from the external controller 12 to the IPG 100, the data is modulated (e.g., encoded) and transmitted by circuitry 120 in the external controller. On the receiving side, this data 170 is received and demodulated (e.g., decoded) using circuitry 125 in the IPG 100. Similarly, when data 172 is to be sent from the IPG 100 to the external controller 12, the data is modulated and transmitted using circuitry 124 in the IPG. On the receiving side, this data 172 is received and demodulated using circuitry 121 in the external controller 12. As mentioned above, one modulation protocol operable in the respective modulation and demodulation circuit blocks 120, 121, 124, and 125 is FSK, which can represent logic '0's and '1's with an appropriate frequency. For example, logic '1' can be modulated with a 129 kHz carrier, while logic '0 can be modulated with a 121 kHz carrier. The inductor-capacitor (LC) tank circuits associated with these links are accordingly tuned to resonate at these frequencies, as is well known.

Unfortunately, the boost converter 150, which also comprises an LC circuit, will also generate a magnetic field 173 when it is enabled, in particular because of the magnetic field generated by the inductor 66. This magnetic field 173 can interfere with the telemetry transmission and reception at coil 13 in the IPG 100. Even if coil 13 has a high quality factor, and good out-of-band noise rejection, the magnetic field 173 may still have frequency components that are within the band of coil 13 (e.g., from 100 kHz to 150 kHz). Moreover, the frequencies components present in magnetic field 173 can have a large bandwidth, and are difficult to control because they depend on the required compliance voltage V+ that must be produced at any given time. Because the IPG 100 usually allows a wide range of stimulation settings to be programmed, the possibility of telemetry interference arising from operation of the boost converter 150 becomes a real possibility. If the interference is severe, telemetry may not be possible during times when the IPG 100 is generating a compliance voltage, i.e., during times that the IPG 100 is operational and producing therapy to the patient, which is unpractical.

Accordingly, the implantable stimulator art would benefit from improved DC-to-DC converter circuitry for adjustably boosting the battery voltage to the compliance voltage needed to provide power to the stimulating electrode(s), while minimizing the effects of magnetic noise that interferes with telemetry operation of the implantable stimulator. Embodiments of such a solution are provided herein.

BRIEF DESCRIPTION OF THE DRAWINGS

FIGS. 1A and 1B show an implantable medical device, and the manner in which an electrode array is coupled to the IPG in accordance with the prior art.

FIG. 2 shows the relation between the implantable medical device and an external controller.

DETAILED DESCRIPTION

The description that follows relates to use of the invention within a spinal cord stimulation (SCS) system. However, it is to be understood that the invention is not so limited. Rather, the invention may be used with any type of implantable medical device system that could benefit from improved compliance voltage generation circuitry.

Improved compliance voltage generation circuitry for a medical device is disclosed. The improved circuitry in one embodiment comprises a boost converter and a charge pump, either of which is capable of generating an appropriate compliance voltage from the voltage of the battery in the implant. The boost converter, which contains at least one inductor, can generate a magnetic field. The charge pump, by contrast, contains no devices capable of generating a substantial magnetic field. In one embodiment, a telemetry enable signal indicating whether the implant's transmitter, receiver, or both, have been enabled is received from the implant's microcontroller. A "boost" signal from compliance voltage monitor-and-adjust logic circuitry is ANDed with the telemetry enable signal and sent to the enable input of the charge pump. The boost signal is ANDed with the inverse of the telemetry enable signal and sent to the enable input of the boost circuitry. So configured, the compliance voltage is generated either by the boost circuitry or the charge pump depending on whether the telemetry enable signal is active: if the telemetry enable signal is not active during a first operational mode, the boost converter is used to generate the compliance voltage; if the telemetry enable signal is active during a second operational mode, the charge pump is used. Because the charge pump circuitry does not produce a magnetic field, the charge pump will not interfere with magnetically-coupled telemetry between the implant and an external controller. By contrast, the higher-efficiency boost converter is allowed to operate during periods of no telemetry, when magnetic interference is not a concern.

Figure 3:
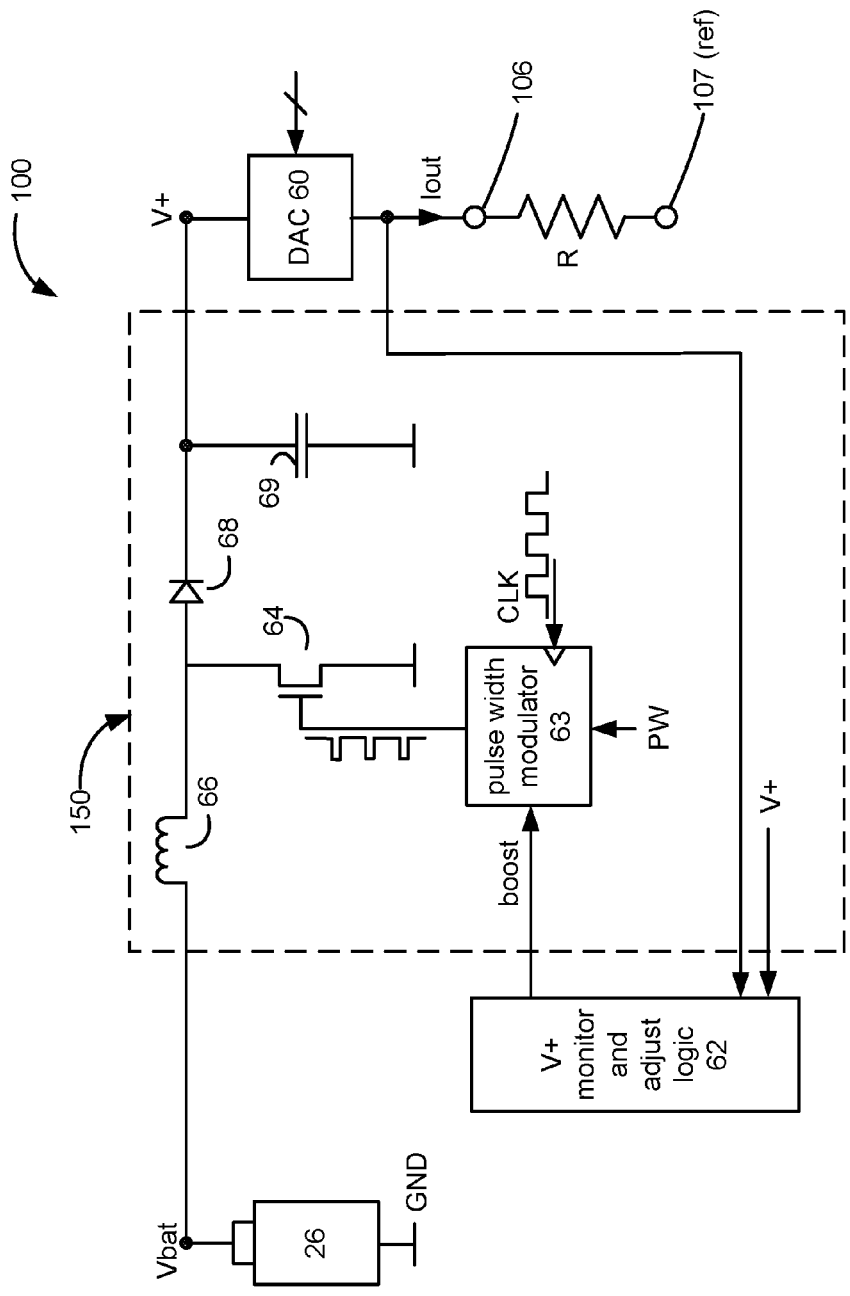
FIG. 3 shows a prior art boost converter circuit for generating a compliance voltage V+ from the battery voltage in an IPG.
Figure 4:
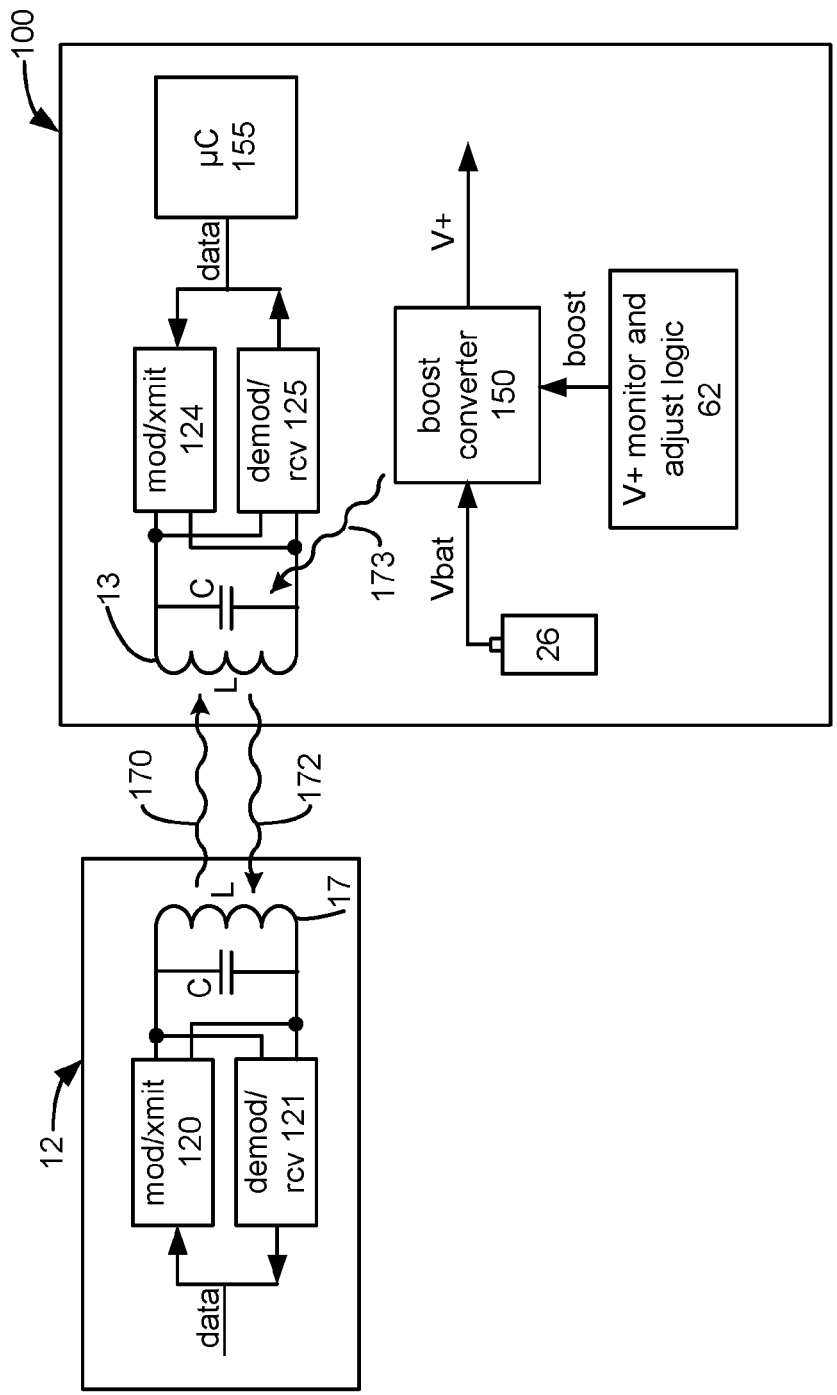
FIG. 4 shows the boost converter of FIG. 3 in conjunction with telemetry circuitry in an IPG, and shows possible interference of the boost circuitry with the telemetry circuitry.
Figure 5:
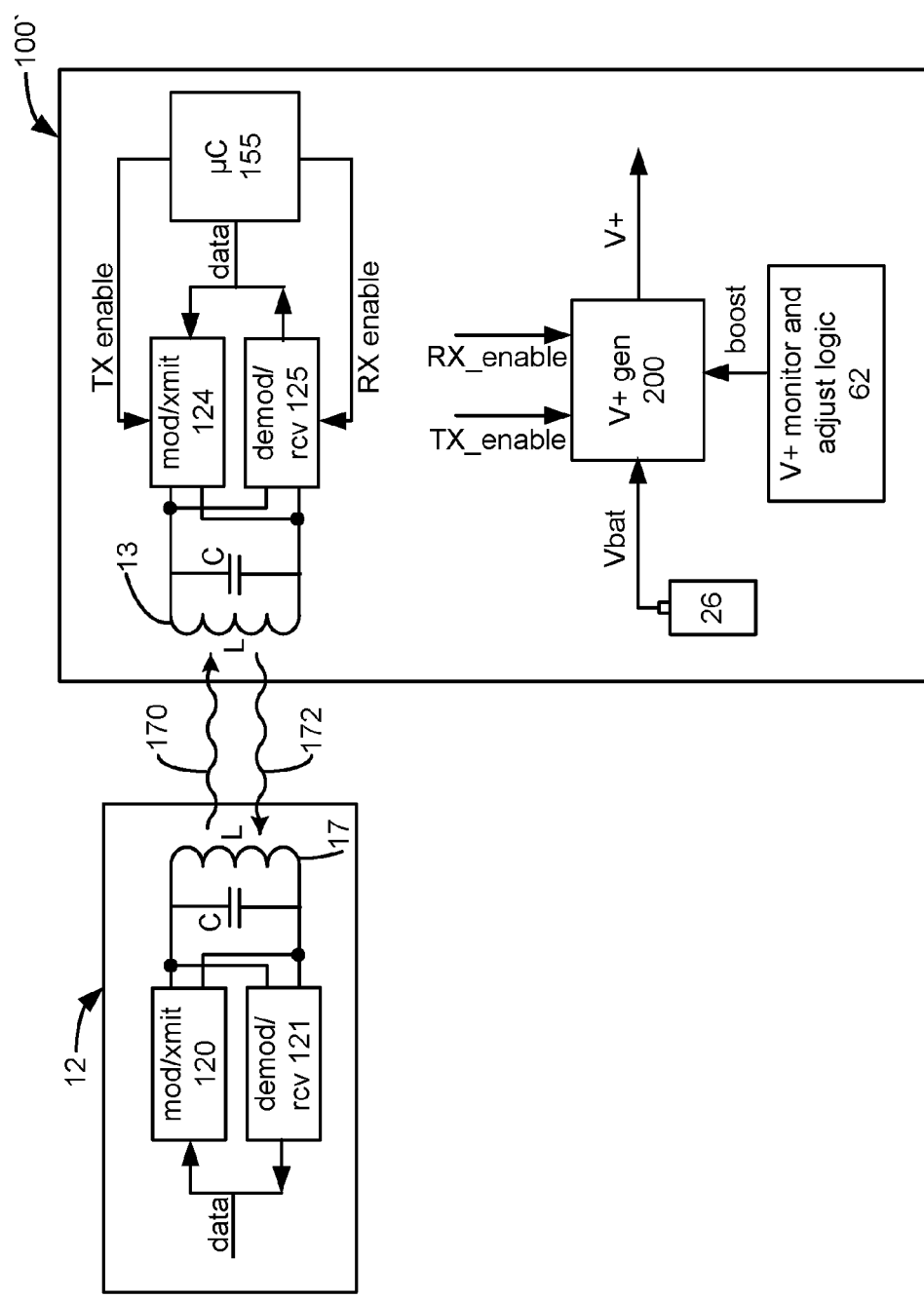
FIG. 5 shows improved V+ generation circuitry in an IPG in accordance with an embodiment of the invention.

An IPG 100' having improved compliance voltage (V+) generation circuitry 200 is shown in FIG. 5. As with the boost converter 150 of the prior art (FIGS. 3-4), the function of V+ generation circuitry 200 is to produce a DC compliance voltage V+ from the battery voltage, Vbat. Also like the prior art, the V+ generation circuitry 200 receives a "boost" signal from V+ monitor and adjust logic 62, such that "boost" is asserted when the logic 62 determines that V+ is too low, and is unasserted when the logic 62 determines that V+ is too high.

However, unlike the prior art, V+ generation circuitry receives a signal or signals indicating the status of telemetry in the IPG 100'. Specifically, in the embodiment shown, V+ generation circuitry 200 receives two signals, TX_enable and RX_enable (collectively, "telemetry enable signals"), which respectively indicate whether transmission of data from the IPG 100' has been enabled and whether reception of data at the IPG 100' has been enabled. The telemetry enable signals generally issue from the microcontroller 155 in the IPG 100', and may already be present in an IPG device. Such telemetry enable signals are traditionally used to selectively enable the modulator 124 and demodulator 125 so that such circuits do not needlessly remain constantly powered, which would drain the battery 26.

Figure 6A:
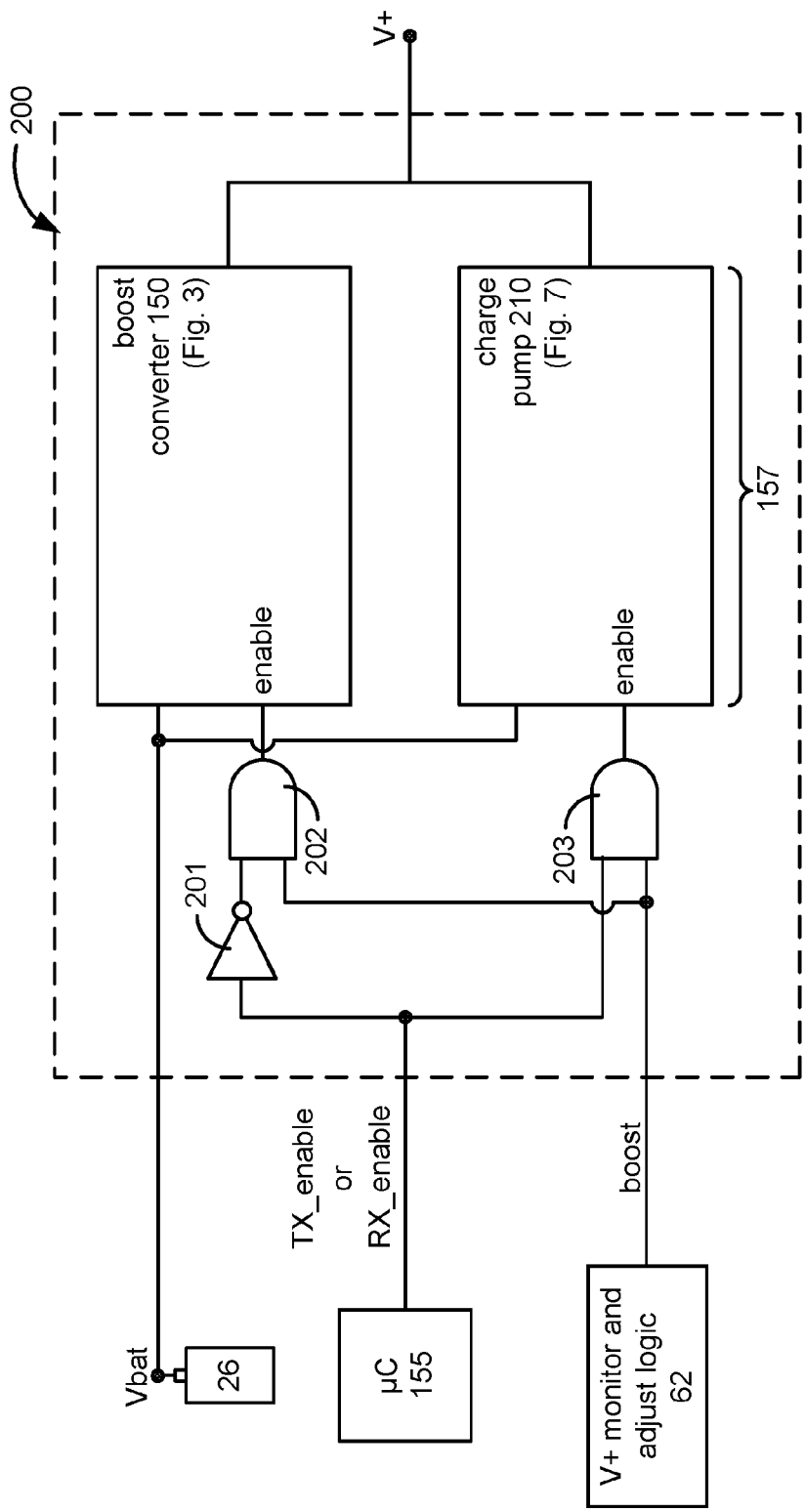
FIGS. 6A and 6B show details of the improved V+ generation circuitry, which includes a boost circuit and a charge pump that are selectable to generate the compliance voltage depending on enablement of telemetry at the IPG.
Figure 7:
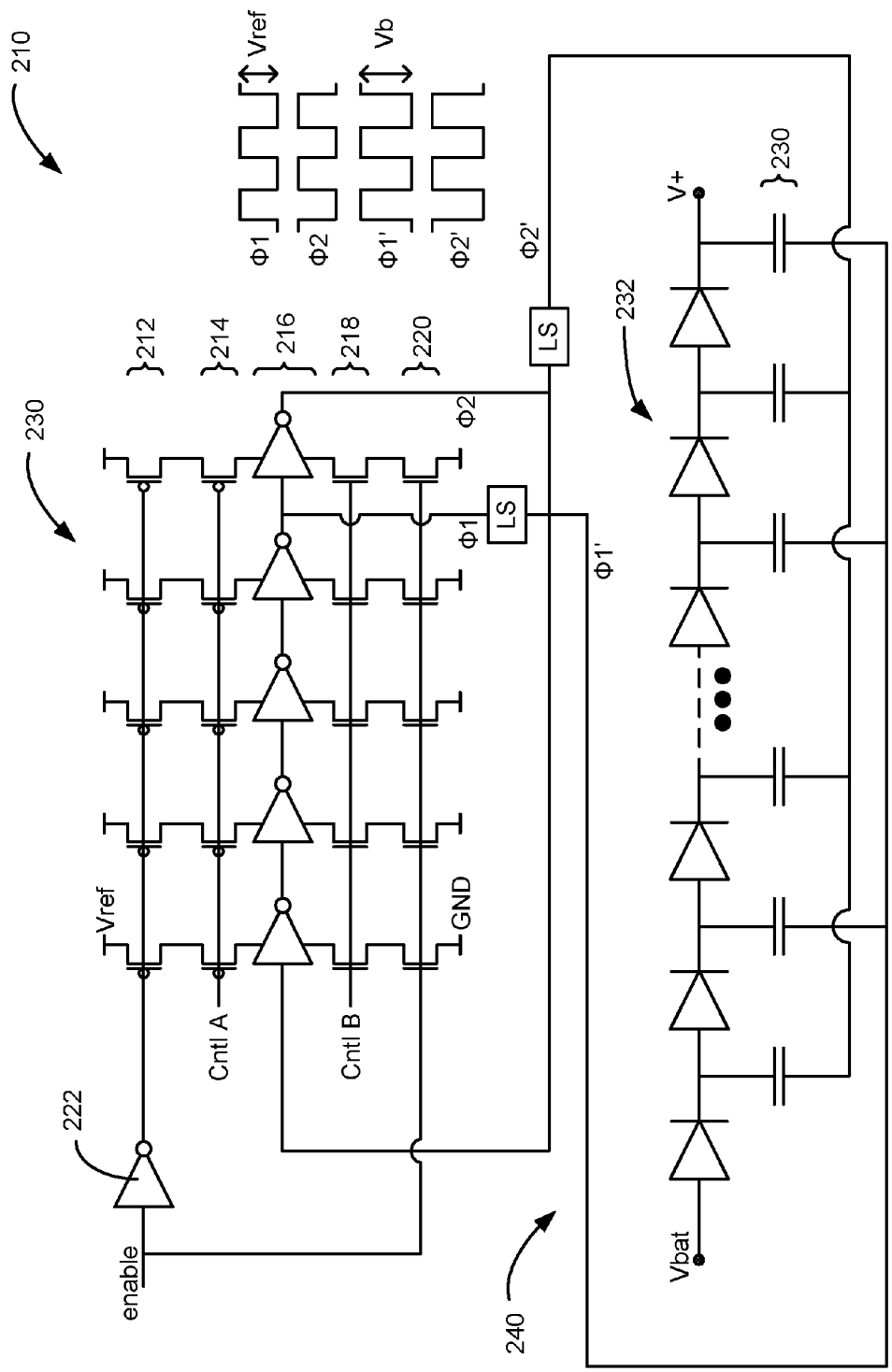
FIG. 7 shows the circuitry for a charge pump useable in the improved V+ generation circuitry of FIGS. 6A and 6B.

Further details concerning the V+ generation circuitry 200 are shown in FIG. 6A. As shown, V+ generation circuitry comprises two different DC-DC conversion circuits 157: a boost converter 150, and a charge pump 210. The boost converter 150 may be the same as discussed in the Background in conjunction with FIG. 3; such details concerning the boost converter are not repeated here. Circuitry useable for the charge pump is shown in FIG. 7, which will be discussed further below. Any buffers or conditioning circuits in the stages 150 and 210 used with respect to the input voltages (e.g., Vbat) or the output voltage (e.g., V+) are omitted.

As mentioned above, V+ generation circuitry 200 receives the "boost" signal from the V+ monitor and adjust logic circuitry 62, which circuitry can remain unchanged from the prior art. Additionally, either the TX_enable signal, the RX_enable signal, or both, are received at the V+ generation circuitry 200 to control the operation of the boost converter 150 and the charge pump 210. Which of these telemetry enable signals are used depends on the telemetry mode of concern to the designer. For example, if the designer is only concerned about potential magnetic interference emanating from the V+ generation circuitry 200 during periods when the IPG 100' is receiving data, then only the RX_enable signal needs to be used (FIG. 6A). If interference is a concern only during transmission of data from the IPG 100', then only the TX_enable signal needs to be used (FIG. 6A). If interference is of concern during both reception and transmission, then both enable signals would be used (FIG. 6B).

The role of the telemetry enable signal(s) in the V+ generation circuitry 200 is to allow only one of the boost converter 150 and the charge pump 210 to be enabled at any given time. To effectuate this, and as shown in FIG. 6A, the relevant telemetry enable signal (assuming only one is used), is inverted using an inverter 201. The inverted version of the telemetry enable signal is logically ANDed with the "boost" signal from V+ monitor and adjust logic circuitry 62 at AND gate 202, whose output is sent to the enable input of the boost converter 150 (e.g., the input to the pulse width modulator 63 of FIG. 3). The non-inverted version of the telemetry enable signal is logically ANDed with the "boost" signal from V+ monitor and adjust logic circuitry 62 at AND gate 203, whose output is sent to the enable input of the charge pump 210 (FIG. 7).

Assume that the V+ generation circuit 200 only receives RX_enable because interference with data reception is the designer's sole concern. The effect of the various logic gates in FIG. 6A is to enable the charge pump 210 and disable the boost converter 150 when a compliance voltage needs to be generated ("boost") and when the IPG is enabled for the reception of data. By contrast, the logic gates enable the boost converter 150 and disable the charge pump 210 when a compliance voltage needs to be generated ("boost") and when the IPG is not enabled for reception.

Figure 6B:
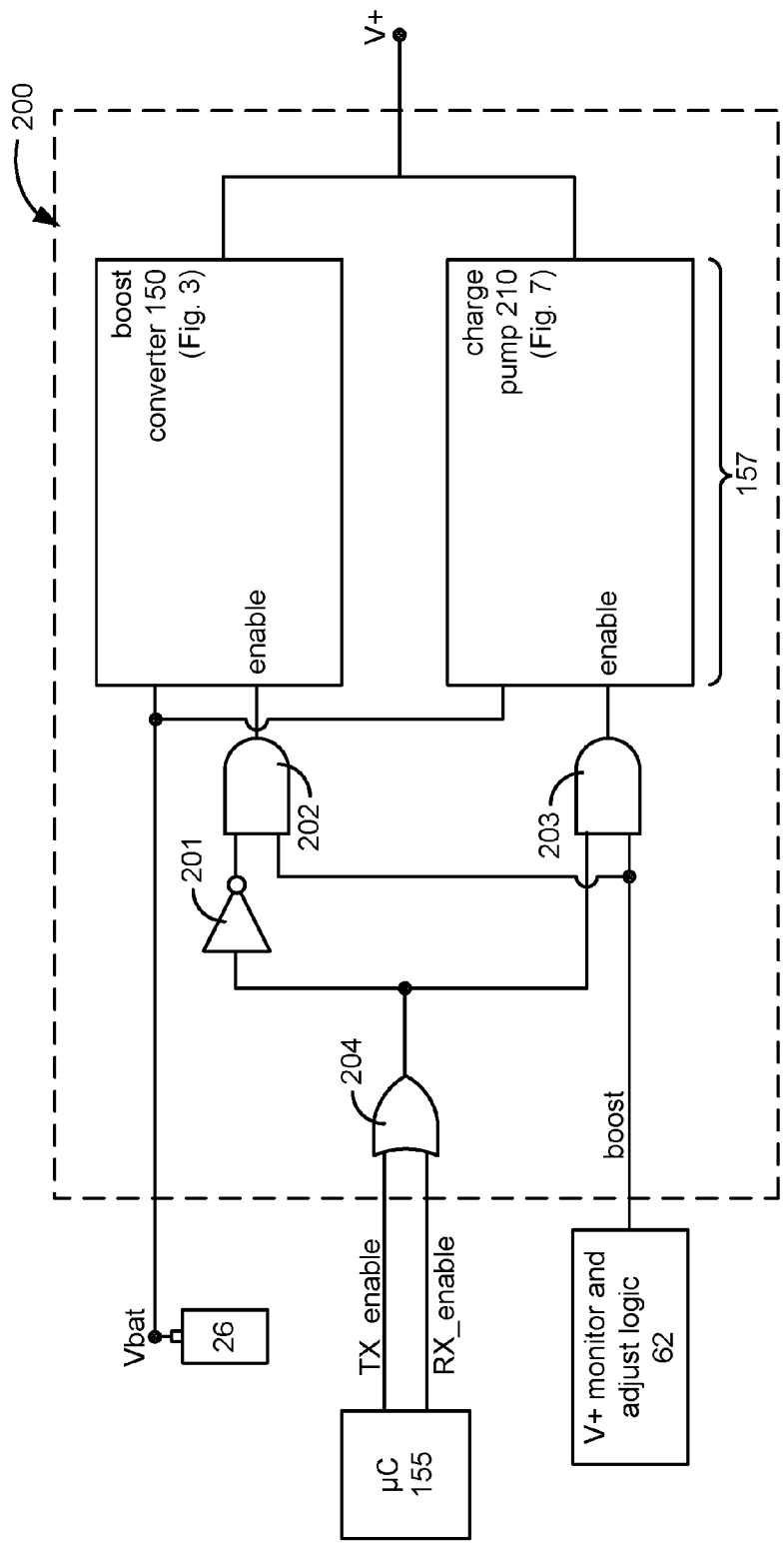

If such selective control of the enablement of the boost convert 150 and the charge pump 210 is desired when transmitting and receiving, then the circuitry of FIG. 6B can be used. In this circuit, the TX_enable and RX_enable signals are logically ORed at OR gate 204, whose inverted and non-inverted output is sent to AND gates 202 and 203 respectively. The effect is to enable the charge pump 210 and disable the boost converter 150 when a compliance voltage needs to be generated ("boost") and when the IPG is enabled for either the reception or transmission of data. By contrast, the boost converter 150 is enabled and the charge pump 210 is disabled when a compliance voltage needs to be generated ("boost") and when the IPG is not enabled for either reception or transmission.

Example circuitry useable for the charge pump 210 in the V+ generation circuitry 200 is shown in FIG. 7. In the example shown, the charge pump 210 comprises a ring oscillator 230 and a capacitor-diode bank 240. The ring oscillator 230 comprises an odd number of inverters 216 serially connected in a ring. The inverters 216 are coupled to power supply voltages Vref (which may comprise a stable voltage such as that provided by a band gap generator) and ground via transistors 212, 214, 218, and 220. P-channel transistors 212 and N-channel transistors 220 respectively receive inverted and non-inverted versions of the enable signal (from AND gate 203 in FIGS. 6A and 6B), such that when the enable signal is high, these transistors are on and able to couple the power supply voltages to the inverters 216. Intervening P-channel transistors 214 and N-channel transistors 218 receive analog control signals "Cntl A" and "Cntl B," whose levels are adjustable to turn on transistors 214 and 218 to relative degrees, and to further influence the coupling of the power supply voltages to the inverters 216. Cntl A and Cntl B can be provided by the V+ monitor and adjust logic 62 for example. Thus, assuming the ring oscillator 230 is enabled, the inverters 216 will start to toggle to produce two clocks, φ1 and φ2, which are out of phase, and which have a magnitude of Vref. Level shifters (LS) then modify that magnitude to higher levels Vb to form signals φ1' and φ2'.

These clock signals φ1' and φ2' are sent to the capacitor-diode bank 240, which comprises a plurality of capacitors 230 separated by diodes 232. Specifically, φ1' is sent the bottom plates of the even numbered capacitors, while φ2' is sent to the bottom plates of the odd numbered capacitors. As is well known, this arrangement allows the input voltage, Vbat, to be boosted to a value V+=Vbat+N(Vb−Vd)−Vd, where Vd comprise the voltage drop across one of the diodes 232, and N equals the number of stages in the bank. Therefore, by controlling either N or Vb, the magnitude of the compliance voltage V+ can be set to an appropriate value. For example, switches (not shown) could be provided to bypass any of the N stages in the capacitor-diode bank 240.

In an alternative implementation, the compliance voltage V+ produced by the charge pump 210 is not adjustable. Instead, when the charge pump 210 is enabled, the charge pump simply produces a maximum compliance voltage (V+$_{max}$) sufficient to handle the power requirements demanded of the IPG 100. This alternative renders the charge pump 210 simpler and alleviates complexity in controlling the charge pump. However, the power provided by V+$_{max}$ may be excessive for the amount of therapeutic current to be provided by IPG 100 at any given moment. As noted earlier, this is generally wasteful of the battery 26's power. However, this power-efficiency problem is mitigated when one recognizes that the charge pump 210 can be expected to operate infrequently, a point discussed further below.

While FIG. 7 illustrates an exemplary controllable charge pump useable to generate a desired compliance voltage, note that other capacitor-based circuits are useable in this regard. See, e.g., the '884 patent, incorporated above.

Unlike the boost circuitry 150, the capacitor-based charge pump 210 of FIG. 7 does not contain any components (like inductors) capable of producing a significant magnetic field. As such, the charge pump 210 can operate to produce the compliance voltage without producing magnetic fields which could interfere with the magnetically-coupled telemetry link between the IPG 100' and the external controller 12. This is the rationale of the disclosed technique for using the charge pump 210, instead of the boost converter 150, to generate the compliance voltage, V+, during periods of telemetry.

One drawback to the use of the disclosed technique is that a charge pump 210 may be less efficient than a boost converter 150 from a power consumption standpoint, particularly if the charge pump is not designed to be adjustable and to output a maximum voltage, V+$_{max}$ as discussed above. Thus, the charge pump 210 may draw more power from the rechargeable battery 26 in the IPG 100' than would the boost converter 150. However, this lack of efficiency is mitigated when it is realized that telemetry occurs relatively infrequently during the operation of the IPG 100'. For example, while the IPG 100' may provide therapeutic currents to the patient essentially continuously, telemetry may need to occur for only minutes or seconds a day. Therefore, the charge pump 210 would typically only operate to (inefficiently) generate a compliance voltage for a relatively short period, with the boost converter 150 generating the compliance voltage for the remainder of the time not requiring telemetry. This overall effect of the inefficiency of the charge pump 210 therefore should have minimal effect on the capacity of the battery 26.

Another drawback of the disclosed technique relates to electrical noise: while the charge pump 210 does not create appreciable magnetic noise, it does create electrical noise due to the high degree of high frequency switching that occurs in its circuitry. Such electrical noise could affect other circuits present on the application specification integrated circuit (ASIC) on which the charge pump 210 is typically formed. However, as one skilled in the art will appreciate, such electrical noise can be mitigated intelligently laying out the charge pump on the ASIC, and by buffering the charge pump with appropriate isolation circuitry.

Figure 8:
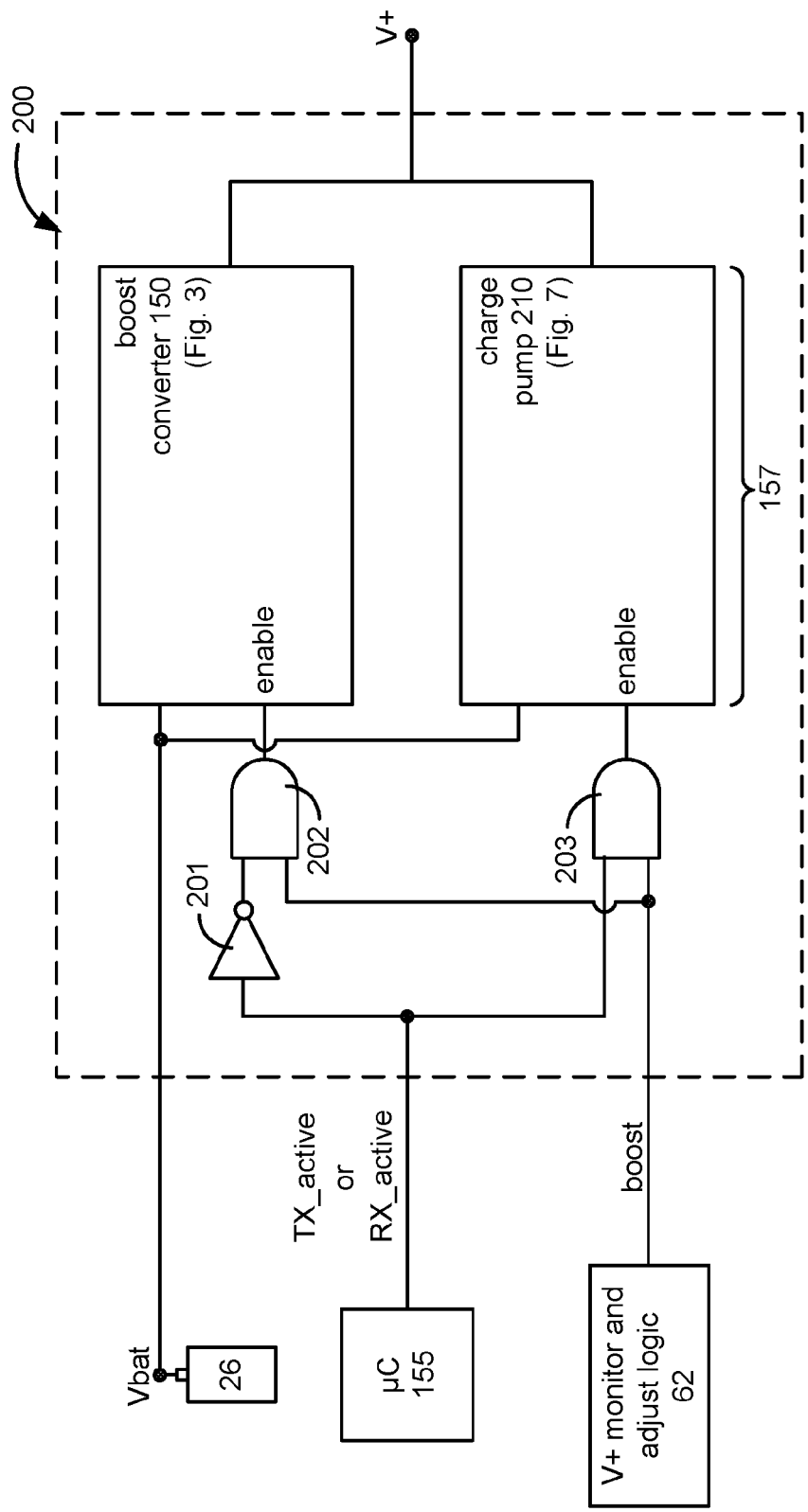
FIG. 8 shows an alternative embodiment for the improved V+ generation circuitry which uses signals indicative of actual telemetry instead of enabled telemetry.

In the disclosed embodiments, telemetry enable signals (TX_enable, RX_enable, or both) were disclosed as the means for selectively controlling either the charge pump or the boost converter. However, the invention is not so limited. Consider for example the situation in which reception is enabled, i.e., the demodulator 125 in the IPG 100' has received the RX_enable signal and is prepared for reception, but no data has yet arrived at the IPG 100'. If the IPG 100' is merely waiting for data, but the data has not yet arrived, it may be reasonable to operate the boost converter 150, because the risk of magnetic interference is mitigated in the absence of actual data. Therefore, instead of telemetry enable signals, the disclosed technique can use signals which indicate time periods in which data is actually being received or transmitted by the IPG 100' (as opposed to when it is merely enabled to do so). Thus, and as shown in FIG. 8, the enable signals can be replaced by signals which indicate when data is actually being transmitted or received (TX_active, RX_active). As one skilled in the art will realize, such "actual" signals are easily generated by the IPG 100'.

Figure 9:
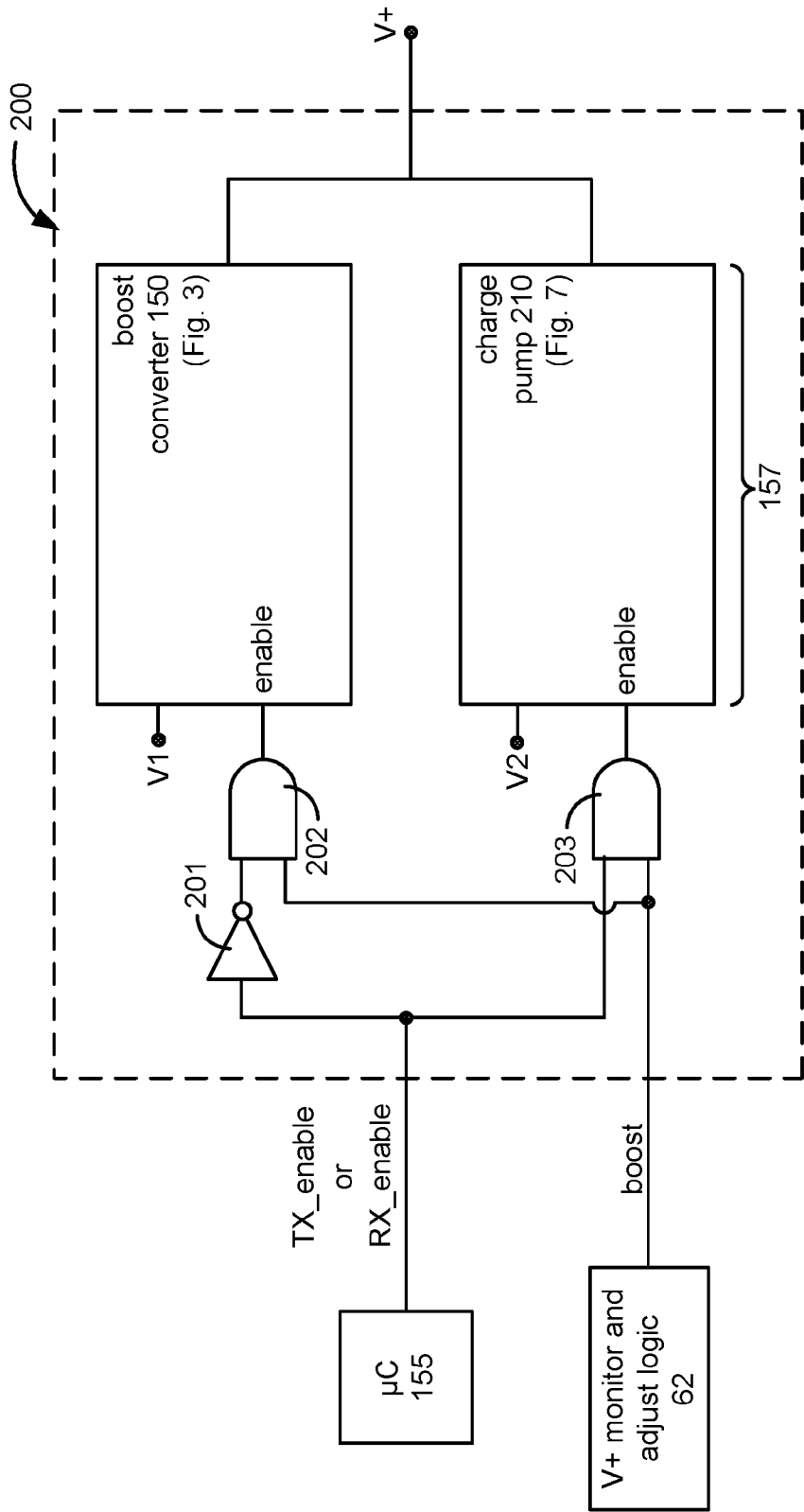
FIG. 9 shows another alternative embodiment for the improved V+ generation circuitry in which the boost circuit and the charge pump receive different input voltages.

Another modification is shown in FIG. 9, which shows that the two boost converter 150 and charge pump 210 stages do not need to receive the same voltage (e.g., Vbat) at their input. Instead, these stages can respectively convert different voltages, V1 and V2, to the compliance voltage, V+. In this case, either V1 or V2 could comprise the battery voltage, Vbat, or could comprise different voltages altogether, including different voltages generated from Vbat. Using different voltages (i.e., a higher voltage) could be beneficial to reduce the amount of voltage boosting that one of the stages needs to provide, or could be useful in the event that it might be desired to isolate one or both of the stages from Vbat.

The disclosed embodiments for V+ generation circuitry 200 were conceived as useful to reduce magnetic interference with the magnetically-coupled telemetry link typically supported by a typical implantable medical device. However, the invention should not be understood as being so limited. Many different types of interference are possible in an implanted medical device, and there may be many different reasons to desire to use one of a plurality of types of DC-DC converter circuits depending on the status of telemetry in the implant. Therefore, it is not important to the scope of the invention that a boost converter or charge pump be used, but instead only that two different types of DC-DC converter circuits be selectable depending on the status of telemetry. It is also not important that the telemetry link be a magnetically-coupled link. For example, if the telemetry link is electromagnetic, such as a link carrying a typical cell phone- or Wifi-type protocol, or other short-range communication protocol, what may be more important is the selection of a DC-DC converter circuit which is less prone to interfering with such a link.

Moreover, selection of a given DC-DC converter circuit may not hinge on the reduction of interference at all, and may be made on the basis of factors other than telemetry. For example, selection of one of a plurality of different types of DC-DC converter circuits may be made of the basis of power efficiency, rather than concerns about telemetry interference.

Finally, the DC-DC converter circuits need not boost the battery voltage directly. Instead, embodiments of the invention can be used to boost any first voltage to a compliance voltage, regardless of whether the first voltage is or is derived from the battery voltage.

Although disclosed in the context of an implantable medical device, embodiments of the disclosed techniques can also be implemented in an external medical device. For example, the disclosed technique could be used with an external trial stimulator, such as is typically used to mimic operation of an implantable stimulator during a trial period in which only electrode leads have been implanted. Additionally, the disclosed techniques are useable in non-medical contexts as well.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical device, comprising:
   electrodes configured to stimulate a patient's tissue;
   a first converter circuit configured to convert a first voltage to a compliance voltage when enabled; and
   a second converter circuit configured to convert the first voltage to the compliance voltage when enabled,
   wherein the first converter circuit and second converter circuit are not configured to be simultaneously enabled, and
   wherein the compliance voltage is configured to provide power for the electrodes to provide stimulation at the patient's tissue.

2. The device of claim 1, further comprising power circuitry configured to receive the compliance voltage.

3. The device of claim 2, wherein the power circuitry comprises current generation circuitry configured to provide a stimulation current to at least one of the electrodes.

4. The device of claim 1, wherein the first converter circuit is configured to be enabled by a signal, and the second converter circuit is configured to be enabled by the inverse of that signal.

5. The device of claim 4, further comprising control circuitry, wherein the control circuitry is configured to issue the signal.

6. The device of claim 1, wherein the first converter circuit is configured to be enabled when a boost signal and at least one telemetry indicator signal are both asserted, and wherein the second converter circuit is configured to be enabled when the boost signal and the inverse of the at least one telemetry indicator signal are both asserted.

7. The device of claim 1, further comprising circuitry configured to monitor and adjust the compliance voltage, wherein the circuitry configured to monitor and adjust the compliance voltage is configured to issue the boost signal.

8. The device of claim 1, wherein the first converter circuit is configured to be enabled when the medical device is ready to transmit or receive data.

9. The device of claim 8, wherein the second converter circuit is configured to not be enabled when the medical device is ready to transmit or receive data.

10. The device of claim 1, wherein the first converter circuit is configured to be enabled when the medical device is actually transmitting or receiving data.

11. The device of claim 10, wherein the second converter circuit is configured to not be enabled when the medical device is actually transmitting or receiving data.

12. The device of claim 1, wherein the first converter circuit is configured to be enabled during periods of telemetry to or from the medical device, and wherein the second converter circuit is configured to be enabled during periods of no telemetry to or from the medical device.

13. The device of claim 1, wherein the first converter circuit is configured to be enabled during a first medical device operational mode, and wherein the second converter circuit is configured to be enabled during a first medical device operational mode.

14. The device of claim 13, wherein the first medical device operational mode comprises telemetry and stimulation, and wherein the second medical device operational mode comprises stimulation without telemetry.

15. The device of claim 1, wherein the first converter circuit does not contain an inductor, and wherein the second converter circuit does contain an inductor.

16. The device of claim 1, wherein the first converter circuit comprises a capacitor-based change pump, and wherein the second converter circuit comprises an inductor-based boost converter.

17. The device of claim 1, further comprising a feedback loop configured to adjust the compliance voltage.

* * * * *